(12) United States Patent
York et al.

(10) Patent No.: US 7,879,572 B2
(45) Date of Patent: Feb. 1, 2011

(54) REGULATION OF $F_1$-ATPASE BETA SUBUNIT CELLULAR LOCATION

(75) Inventors: David A. York, Logan, UT (US); MieJung Park, Logan, UT (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 625 days.

(21) Appl. No.: 11/719,175

(22) PCT Filed: Oct. 19, 2005

(86) PCT No.: PCT/US2005/037779

§ 371 (c)(1),
(2), (4) Date: May 11, 2007

(87) PCT Pub. No.: WO2006/055167

PCT Pub. Date: May 26, 2006

(65) Prior Publication Data
US 2009/0208976 A1 Aug. 20, 2009

Related U.S. Application Data

(60) Provisional application No. 60/627,455, filed on Nov. 12, 2004.

(51) Int. Cl.
*G01N 33/573* (2006.01)
(52) U.S. Cl. .......................................... 435/7.4; 435/18
(58) Field of Classification Search ........................ None
See application file for complete search history.

(56) References Cited

U.S. PATENT DOCUMENTS 5,264,372 A * 11/1993 Beaumont et al. ........... 436/504

OTHER PUBLICATIONS

Clare D.A. and Swaisgood H.E. Bioactive milk peptides: A prospectus, Journal of Dairy Science, 2000, vol. 83, No. 6, pp. 1187-1195.*
Goeser T. et al. The rat hepatocyte plasma membrane organic anion binding protein is immunologically related to the Mitochondrial F1 Adenosine triphophatase beta-subunit, Journal of Clinical Investigation, 1990, vol. 86, pp. 220-227.*
Berger K. et al., Mitochondrial ATP synthase—a possible target protein in the regulation of energy metabolism in vitro and in vivo, *Nutr Neurosci*, vol. 5, pp. 201-210 (2002).
Chang S. et al., "Interaction of the C-terminal domain of p43 and the α-subunit of ATP synthase: its functional implication in endothelial cell proliferation," *J. Biol. Chem.*, vol. 277, pp. 8388-8394 (2001).
Lin L. et al., "Enterostatin inhibition of dietary fat intake is dependent upon CCKA receptors," *Am. J. Physiology*, vol. 285, No. 2, pp. R321-R328 (Aug. 2003).
Lin, L. et al., "Enterostatin suppresses food intake in rats after near celiac and intracarotid arterial injection," *Am. J. Physiol. Reg Integr Comp Physiol*, vol. 278, No. 5, pp. R1346-R1351 (2000).
Martinez Lo et al., "Ectopic beta-chain of ATP synthase is an apolipoprotein A-I receptor in hepatic HDL endocytosis," *Nature* (Lond) vol. 421, pp. 75-79 (2003).
Moser, T.L. et al., "Angiostatin binds ATP synthase on the surface of human endothelial cells," *Proc. Natl. Acad. Sci.*, vol. 96, pp. 2811-2816 (1999).
Ookuma, M. et al., "Inhibition of insulin release by enterostatin," *Int. J. Obesity*, vol. 22, pp. 800-805 (1998).
Park, M. et al., "The $F_1$-ATPase β-subunit is the putative enterostatin receptor," *Peptides*, vol. 25, pp. 2127-2133 (2004) Available online Oct. 19, 2004.
White C.L. et al., "Intragastric beta-casomorphin$_{(1-7)}$ attenuates the suppression of fat intake by enterostatin," *Peptides*, vol. 21, pp. 1377-1381 (2000).
Barton C.et al., "Differential effects of enterostatin, galanin and opioids on high-fat diet consumption," *Brain Res.*, pp. 702:55-60 (1995).
Berger K. et al., Binding of enterostatin to the human neuroepithelioma cell line SK-N-MC, *Peptides*, vol. 19, pp. 1525-1531 (1998).
Bowyer, R. C. et al., "The effect of a satiating meal on the concentrations of procolipase activation peptide in the serum and urine of normal and morbidly obese individuals," *Gut.*, vol. 34, pp. 1520-1525 (1993).
Das B. et al., "A novel ligand in lymphocyte mediated cytotoxicity: expression of beta subunit of H+ transporting ATP synthase on the surface of tumor cell lines," *J. Exp. Med.*, vol. 180, pp. 273-281 (1994).
Erlanson-Albertsson, C. et al., "Pancreatic procolipase propeptide, enterostatin, specifically inhibits fat intake," *Physiol. Behav.*, vol. 49, pp. 1191-1194 (1991).
Erlanson-Albertsson, C. et al., "A possible physiological function of procolipase activation peptide in appetite regulation," *Biochimie*, vol. 70, pp. 1245-1250 (1988).
Erlanson-Albertsson, C. et al., "Enterostatin—A peptide regulating fat intake," *Obesity Res*, vol. 5, pp. 360-372 (1997).

(Continued)

*Primary Examiner*—Jon P Weber
*Assistant Examiner*—Satyendra K Singh
(74) *Attorney, Agent, or Firm*—Bonnie J. Davis; John H. Runnels (57) ABSTRACT

It has been discovered that the ability of analogues to affect binding of a labeled β-casomorphin (an enterostatin antagonist) to recombinant rat $F_1$-ATPase β-subunit was closely correlated with their enterostatin-like biological activity. Using immunohistochemistry and western blots, the presence of the $F_1$-ATPase β-subunit was demonstrated in plasma membranes of liver, pancreas and amygdala. The effects of enterostatin on the intracellular localization of the proteins were studied using deconvolution or confocal microscopy. Enterostatin did not alter the location of $F_1$-ATPase a-subunit-RFP but induced movement of the $F_1$-ATPase β-subunit-GFP to the periphery of cells. These studies, showing the plasma membrane localization of the $F_1$-ATPase β-subunit, the influence of enterostatin on the cellular location of the protein, the appropriate Kd value for binding, together with the previous correlation of binding effects with biological activity for a number of analogues, indicate that this protein is the enterostatin receptor.

5 Claims, 5 Drawing Sheets

OTHER PUBLICATIONS

Halford, J et al., "Serotonin (5HT) and Serotoninergic Receptors in the Regulation of Macronutrient Intake," Nural and Metabolic Control of Macronutrient Intake, eds HR Berthoud and RJ Seeley, pp. 425-446 CRC Press, Boca Raton (2000).

Imamura, M. et al., "Distribution and characterization of enterostatin-like immunoreactivity in human cerebrospinal fluid," *Peptides*, vol. 19, pp. 1385-1391 (1998).

Lin L. et al., "Procolipase gene and enterostatin expression in the rat brain," FASEB J, p. A783 (2002).

Lin L. et al., "Amygdala enterostatin induces c-Fos expression in regions of hypothalamus that innvervate the PVN," *Brain Res.* 2004 vol. 1020(1-2), pp. 147-153 (Sep. 2004).

Lin, L. et al., "Chronic ICV Enterostatin Preferentially Reduced Fat Intake andf Lowered Body Weight," *Peptides*, vol. 18, pp. 657-661 (1997).

Lin, L. et al., "Effect of enterostatin on the feeding responses to galanin and NPY," *Obes. Res.*, vol. 1, pp. 186-192 (1993).

Lin, L. et al., "Beta-casomorphins stimulate and enterostatin inhibits the intake of dietary fat in rats," *Peptides*, vol. 19, pp. 325-331 (1998).

Lin, L. et al., "Enterostatin actions in the amygdala and PVN to suppress feeding in the rat," *Peptides*, vol. 18, pp. 1341-1347 (1997).

Lin, L. et al., "Changes in the microstructure of feeding after administration of enterostatin into the paraventricular nucleus and the amygdala," *Peptides*, vol. 19, pp. 557-562 (1998).

Lin, L. et al., "Comparisons of the effects of enterostatin on food intake and gastric emptying in rats," *Brain Res,*, vol. 745, pp. 205-209 (1997).

Lin, L. et al., "Structural requirements for the biological activity of enterostatin," *Peptides*, vol. 15, pp. 849-854 (1994).

Mei J et al., "Inhibition of insulin releases by intraduodenally infused enterstatin-VPDPR in rats," *Peptides* vol. 18, No. 5, pp. 651-655 (1997).

Mei, J. et al., "Identification of enterostatin, the pancreatic procolipase activation peptide, in the intestine of rat: effect of CCK-8 and high-fat feeding," *Pancreas*, vol. 8, pp. 488-493 (1993).

Mei, J. et al., "Erlanson-Albertsson, C., Enterostatin—its ability to inhibit insulin secretion and to decrease high-fat food intake," *Int. J. Obesity*, vol. 17, pp. 701-704 (1993).

Mei, J. et al., "Effect of enterostatin given intravenously and intracerebroventricularly on high-fat feeding in rats," *Regul. Pept.*, Voo. 41, pp. 209-218 (1992).

Mei, J. et al., "Plasma insulin response to enterostatin and effect of adrenalectomy in rat," *Obes. Res.*, vol. 4, pp. 513-519 (1996).

Mei, J. et al., "Role of intraduodenally administered enterostatin in rat: inhibition of food intake," *Obes. Res.*, vol. 4, pp. 161-165 (1996).

Miner, J. L. et al., "Reduction of feed intake in sheep by enterostatin, the procolipase activation peptide," *J. Anim. Sci., vol.* 72, pp. 1578-1582 (1994).

Nagase H. et al., "Regulation of feeding behavior, gastric emptying, and sympathetic nerve activity to interscapular brown adipose tissue by galanin and enterostatin: the involvement of vagal-central nervous system interactions," *J. Gastroenterol.*, vol. 37, Suppl 14, pp. 118-127 (2002).

Nagase H. et al., "Effect of galanin and enterostatin on sympathetic nerve activity to interscapular brown adipose tissue," *Brain Res.*, vol. 709, pp. 44-50 (1996).

Okada S. et al., "Procolipase mRNA: Tissue localization and effects of diet and adrenalectomy," *Biochem. J.*, vol. 292, pp. 787-789 (1993).

Okada, S. et al., "Chronic effects of intracerebral ventricular enterostatin in Osborne-Mendel rats fed a high-fat diet," *Physiol. Behav.*, vol. 54, pp. 325-330 (1993).

Okada, S. et al., "Differential inhibition of fat intake in two strains of rat by the peptide enterostatin," *Amer. J. Physiol.*, vol. 262, pp. R1111-R1116 (1992).

Okada, S. et al., "Enterostatin (Val-Pro-Asp-Pro-Arg) the activation peptide of procolipase selectively reduces fat intake," *Physiol. & Behav.*, vol. 49, pp. 1-5 (1991).

Ookuma, K. C. et al., "Effect of enterostatin and kappa-opioids on macronutrient selection and consumption," *Peptides*, vol. 18, pp. 785-791 (1997).

Park, M. et al., "Enterostatin regulates Partitioning of its receptor, the $F_1$-ATPase β-subunit into Plasma Membranes," POSTER, presented at North Am. Assoc. for the Study of Obesity, Las Vegas, NV (Nov. 15, 2004).

Pierzynowski, S. G. et al., "Possible integration of the electrical activity of the duodenum and pancreas secretion through enterostatin," *Biomed. Res.*, vol. 15, pp. 257-260 (1994).

Rippe, C. et al., "Effect of high fat diet, surrounding temperature and enterostatin on uncoupling protein gene expression," *Am. J. Physiol.*, vol. 279; pp. E293-E300 (2000).

Rodriguez-Gallardo J., "Inhibitory effect of enterostatin on the beta cell response to digestive insulinotropic peptides," *Int J Obes Relat Metab Disord*, vol. 23, No. 8, pp. 787-792 (1999).

Rössner, S., et al., "Intravenous enterostatin does not affect single meal food intake in man," *Appetite*, vol. 34, pp. 37-42 (1995).

Smeets, M., P. et al., "The effect of oral enterostatin on hunger and food intake in human volunteers," *FASEB J*, vol. 13, No. 5, p. A871 (1999).

Smith B.K. et al., "Chronic *d*-fenfluramine treatment reduces fat intake independent of macronutrient preference," *Pharmacology Biochem. & Behavior.*, vol. 60, pp. 105-114 (1998).

Sörhede, M. et al., "Enterostatin is produced in three different forms in the rat intestine," *Int. J. Obesity*, vol. 19, p. 115 (1995).

Tadayyon M. et al., "Structure-function studies on enterostatin inhibition of insulin release," *Intl J Diabetes & Metabolism*, vol. 10, pp. 14-21 (2002).

Takenaka Y. et al., "Enterostatin (VPDPR) and its peptide fragment DPR reduce serum cholesterol levels after oral administration in mice," *Biosci. Biotechnol. Biochem.*, vol. 67, pp. 1620-1622 (2003).

Tian, Q. et al., "Vagal-central nervous system interactions modulate the feeding response to peripheral enterostatin," *Obes. Res.*, vol. 2, pp. 527-534 (1994).

Townsley, M. I. et al., "Enterostatin efflux in cat intestinal lymph: Relation to lymph flow, hyaluronan and fat absorption," *Am. J. Physiol.*, vol. 271, pp. G714-G721 (1996).

Weatherford, S. C. et al., "Intraventricular administration of enterostatin decreases food intake in baboons," *Appetite*, vol. 19, p. 225 (1992).

Winzell, M. S. et al., "Rat gastric procolipase: sequence, expression, and secretion during high-fat feeding," *Gastroenterology*, vol. 115, pp. 1179-1185 (1998).

Wu, Y.J. et al., "Comparative study of enterostatin sequence in five rat strains and enterostatin bind proteins in rat and chicken serum," *Peptides*, vol. 23, pp. 537-544 (Mar. 2002).

York, D. A. et al., "Brain amine responses to peripheral enterostatin," *Int. J. Obes.*, vol. 18, p. 102 (1994).

York, D.A. et al., "Enterostatin: A peptide regulator of fat ingestion. In: Pennington Symposium Series, Molecular Biology of Obesity," vol. 4, pp. 281-297 (G.A. Bray and D. Ryan, eds.), Louisiana State University Press, Baton Rouge, USA (1996).

York, D.A. et al., "Enterostatin as a regulator of fat intake," In: Neural and Metabolic Control of Macronutrient selection, H.R. Berthoud and R. J. Seeley (eds.), Chap. 20, pp. 295-308, Boca Raton, FL: CRC Press (2000).

* cited by examiner

Fig. 1A  ATPase beta subunit-GFP construct

Fig. 1B  F1-ATPase alpha subunit-RFP construct

Deconvolution microscopy either with or without fluorescence filter. The effect of either 0.5 uM (1-4) or 2uM enterostatin (5-8) on the localization of expressed beta subunit of $F_1$-ATPase in HepG2 cells (1,5: 0min, 2,6: 15min, 3,7: 30min and 4,8: 60min incubation with enterostatin).

Fig. 2A

Deconvolution microscopy either with or without fluorescence filter. The effect of either 0.5 uM (1-4) or 2uM enterostatin (5-8) on the localization of expressed alpha subunit of $F_1$-ATPase in HepG2 cells (1,5; 0min, 2,6; 15min, 3; 30min and 4; 60min incubation with enterostatin).

Confocal microscopy. The effect of 2uM enterostatin on the localization of expressed beta subunit of $F_1$-ATPase (A) or alpha subunit (B) in HepG2 cells (1-3,7 and 8; 0 min, 4-6; 75min, 9,10; 40min incubation with enterostatin).

$F_1$-ATPase β-subunit Localization in Rat Amygdala, Liver and Pancreas (Western Blot) and Immunohistochemistry (Liver).

1° Ab: α- rabbit rat $F_1$-ATPase beta subunit antibody (1:1000)
2° Ab: α- rabbit IgG peroxidase goat antibody (1:2000)

Western blot (A-C) of $F_1$-ATPase β-subunit in plasma membranes (PM) and mitochondrial membrane (MT) fractions prepared from amygdala (A), liver (B) and pancreas (C) and immunohistochemistry from liver (D)

REGULATION OF $F_1$-ATPASE BETA SUBUNIT CELLULAR LOCATION

This is the United States national stage of international application PCT/US05/37779, filed Oct. 19, 2005, which claims the benefit of the Nov. 12, 2004 filing date of U.S. provisional application Ser. No. 60/627,455 under 35 U.S.C. §119(e).

The development of this invention was partially funded by the Government under a grant from the National Institute of Health (NIDDK45728). The Government has certain rights in this invention.

TECHNICAL FIELD

This invention pertains to a method to regulate the amount of a peptide receptor, the $F_1$-ATPase $\beta$ subunit, in the plasma membrane of mammalian cells, a method to screen patients for response to enterostatin treatment, and a method to screen for compounds that are agonists or antagonists for enterostatin.

BACKGROUND ART

Enterostatin

Enterostatin is the aminoterminal pentapeptide of procolipase that is released by proteolytic activity when procolipase is converted into colipase (9). The procolipase gene is expressed in the exocrine pancreas and the gastric and duodenal mucosa (25, 34, 53). In the gastric mucosa, the gene appears to be concentrated in enterochromaffin cells. More recently, procolipase and enterostatin were shown to be present in specific brain regions including the amygdala and hypothalamus (12).

Enterostatin Effects on Feeding Behavior. The peptide enterostatin has a dose-dependent and selective effect to inhibit fat intake in a number of dietary paradigms. The first criteria for establishing the physiological role of a peptide on feeding behavior is that inhibits food or macronutrient intake in rats adapted to a three-choice macronutrient diet of fat, carbohydrate and protein (7, 36, 37). Enterostatin reduced intake of the fat macronutrient, but had no effect on either carbohydrate or protein intake. In a two-choice high-fat (HF) and low-fat (LF) diet paradigm experiment, enterostatin reduced only intake of the HF diet, but not of the LF diet (15) Similarly, enterostatin reduced intake of single dietary source when the source was HF (17), but not when LF. The ability of enterostatin to selectively inhibit fat intake on a two- or three-choice feeding paradigm has been demonstrated after administration of enterostatin by either intraperitoneal, intracerebroventricular (icv), intraduodenal/intragastric, and near celiac arterial injection (15, 16, 19, 22, 27, 29, 52, 57). Similar to other gut peptides, enterostatin appeared to have at least two sites of action, one in the gastrointestinal tract and one in the central nervous system (20, 49, 57).

While the majority of the feeding studies with enterostatin have been performed in overnight fasted rats that have been previously adapted to the experimental diets, the selective effects towards dietary fat have been shown in free-feeding rats injected at the start of the dark cycle. The potency of enterostatin is reflected in the long duration of action on feeding, lasting up to six hours after a single injection in rats adapted to a six-hour feeding schedule, and lasting up to 24 hours after a single injection in rats adapted to ad-libitum feeding. Chronic icv administration of enterostatin from mini-osmotic pumps also attenuated the daily intake of dietary fat in rats fed either a single-choice HF diet or a two-choice HF/LF diet (15, 35). The decrease in daily food intake was accompanied by a reduction in fat deposition and body weight gain. However, in rats chronically treated with enterostatin and fed a low-fat diet for seven days, no significant reduction was seen in either energy intake or change in body weight gain. An intriguing characteristic of the response to enterostatin in both acute and chronic studies was that the reduction in intake of dietary fat is not compensated by an increase in the intake of other macronutrients when a dietary choice is available. This may result from a concomitant increase in corticotropin releasing hormone (CRH) secretion since enterostatin is known to activate the hypothalamic-pituitary-adrenal (HPA) axis (35).

Enterostatin has also been shown to reduce food intake in rabbits, sheep, and baboons (8, 30, 51). However, all of these studies were performed with single-choice diets. In humans, enterostatin administered by intravenous injection was found to reduce the subjective feeling of hunger (44), although has not been found to reduce food intake (43).

Enterostatin effects on fat intake appear to be expressed at both gastrointestinal and central nervous system (CNS) sites. The response to peripherally-administered enterostatin was found to be mediated through the hepatic vagus nerve; the response was abolished by either selective hepatic vagotomy or capsaicin treatment (32, 49). Within the CNS, enterostatin was found to act on both the amygdala and paraventricular nucleus (PVN) (12, 14, 20). Enterostatin inhibited fat intake by way of a pathway that contained both serotonergic (55) and kappa-opioidergic (38) neurons. Kappa-opioidergic agonists inhibited the enterostatin effects on feeding, and a K-opioidergic antagonist or nor-Binaltorphamine (BNI) mimicked the effect of enterostatin on selective fat intake (1, 38). In contrast, the general serotonergic antagonist, metergoline but not a 5HT2 receptor antagonist, blocked the response to icv-administered enterostatin (57), and serotonin injections into the PVN inhibited dietary fat intake (10, 45).

A physiological regulator of feeding behavior must be effective at dose levels that are present in the animal. The in vivo concentration of enterostatin has not been established, due to problems in measuring enterostatin. Antibodies that are selective to enterostatin that could be used to analyze tissue levels of enterostatin have been difficult to find. The current values for enterostatin all appear very high, for example, plasma serum enterostatin of 5-40 nM in humans (4) and rats, cerebral spinal fluid enterostatin of 18-92 ng/ml, and brain enterostatin levels of 2.5 nmoles/g tissue (11). A suggestion of the existence of multiple forms of enterostatin in rats and in humans because of genetic polymorphisms in the enterostatin region of the procolipase parent molecule further complicates the efforts to measure enterostatin (11, 46). However, other data has disputed the suggestion of multiple forms (53, 54). Despite these measurement problems, enterostatin-like immunoreactivity has been shown to increase both in human serum and urine after a meal in a biphasic manner (4), and in lymph fluid of cats (50) and serum of rats after feeding (9).

Enterostatin regulation of insulin secretion. Several studies have shown that enterostatin inhibits insulin secretion (24, 26, 28, 39, 42, 47). In vivo perfusion of isolated islets and of the rat pancreas has been used to demonstrate that enterostatin directly inhibits insulin release from islet cells induced by either glucose, tolbutamide, or arginine. (39) Enterostatin ($10^{-9}$ to $10^{-5}$ M) inhibited insulin secretion from islets incubated in the presence of 16.7 mM glucose in a dose-dependent manner. Enterostatin also inhibited insulin secretion stimulated by glybenclamide (5.0 and 10 µM), phorbol 12-myristate-13-acetate (TPA) (50 and 100 nM), and the kappa-opioid agonist U50,488 (100 nM). The inhibitory effect of enterostatin on TPA-induced insulin secretion was attenuated, but still remained in the absence of extracellular $Ca^{2+}$. The enterostatin inhibition of insulin secretion was blocked by 8-Br-cAMP (1 mM), independent of extracellular $Ca^{2+}$. Enterostatin reduced the increase in intracellular cyclic AMP content produced by U50,488 (100 nM), in a manner parallel with changes in insulin release (42).

In vivo studies also have shown a reduction in insulin levels without any changes in plasma glucose suggesting an improvement in insulin sensitivity (15, 35). This occurred after both peripheral and central administration of enterostatin, reflecting both direct effects on the islet cells and indirect effects by way of a reduction in vagal stimulation to the pancreas.

Other Effects of Enterostatin. Enterostatin also been shown to affect gastrointestinal motility and gastric emptying (21, 40). The inhibition of gastric emptying was observed only after intracerebroventricular administration of enterostatin, but not after either intraperitoneal or intragastric administration, suggesting that enterostatin also affects efferent vagal activity. However, the inhibitory effect of enterostatin on consumption of a high fat diet was not related to the slowdown of gastric emptying (21). Enterostatin also had direct effects on pig intestine to prolong the quiescent phase I period of peristalsis, which slows down the absorption of nutrients and prolongs intestinal transit time. Enterostatin may also reduce cholesterol levels (48).

Enterostatin also has shown a number of autonomic and endocrine effects in addition to the effect on insulin secretion. It enhanced corticosterone secretion (35) and sympathetic stimulation to brown adipose tissue (32, 33), which would increase thermogenesis (41). These responses, in addition to the suppression of dietary fat intake, help explain the reduction in weight gain and body fat that was seen in rats treated chronically with either peripheral or central enterostatin (15, 35).

Circulating enterostatin. Enterostatin absorption across the intestine was found to be limited and slow, occurring mainly into lymphatic system. Detailed information of the changes in plasma enterostatin or brain uptake of enterostatin after a meal currently exist that would allow a temporal comparison with the termination of feeding and the development of satiety. The data that are available indicate the rise in plasma immunoreactive-like enterostatin activity is slow and does not peak until at least 60 minutes after feeding, which is inconsistent with a theory that an increase in circulating enterostatin plays a role in the termination of the immediate meal.

The presence of procolipase mRNA in the CNS together with enterostatin-like immunoreactivity has been demonstrated, (12, Lin and York, unpublished observations). Enterostatin also was found at high levels in the cerebrospinal fluid of rats. A hypothesis that this central system is important in determining the appetite for dietary fat is consistent with the evidence that endogenous production of enterostatin is reciprocally related to voluntary selection of fat across and within rat strains.

Enterostatin Receptors. Based on the areas responding to enterostatin, receptors would be expected to be located in brain, pancreas, and the gastrointestinal tract. Enterostatin has been shown not to bind to the galanin or Neuropeptide Y1 receptors (17), kappa-opioid receptors or cholecystokinin A receptors (13) Low affinity enterostatin binding was shown to a brain membrane preparation (Kd 230 nM) (56) and to SK-N-MC neuroepithelioma cells (Kd 40 nM) (2). The dose-response curve to enterostatin is biphasic, exhibiting an inhibition of food intake at lower doses, but stimulation of food intake at higher doses (22). However, since enterostatin has been shown to be biologically active on food intake at extremely low doses compared to other peptides and to inhibit insulin secretion from isolated pancreatic islets at doses of $10^{-10}$ to $10^{-6}$ M, a proposed low affinity casomorphin binding site probably is not the biologically important enterostatin receptor that inhibits fat intake and insulin secretion.

The $F_1$ ATPase Receptor. Studies using classical affinity chromatography have identified a binding protein for enterostatin from rat brain membrane fractions (2). The receptor was identified as the β subunit of the $F_1$-ATP synthase, an enzyme normally found in mitochondrial membranes. This protein has been found in the plasma membranes of immortalized human hepatocytes, HepG2 cells, primary human hepatocytes, lymphocytes, and endothelial cells. (5, 6, 23, 31). In endothelial cells, the enzyme probably acts as an ATPase rather than an ATP synthase. On liver cells, the beta subunit was found to bind ApoA-1 and to regulate endocytosis of high density lipoprotein (HDL) particles. (23). The $F_1$-ATPase of lymphocytes and endothelial cells was found to bind angiostatin, and speculated to have a role in angiogenesis. (31). The inhibition of insulin secretion from INS-1 cells by enterostatin has also been related to a reduction in ATP levels (2).

DISCLOSURE OF INVENTION

We have investigated that the binding activity of the purified protein with a labeled antagonist, β-casomorphin (18, 52), in the absence and presence of cold enterostatin. (See Appendix B) $^{125}$I-β-casomorphin weekly binds to rat $F_1$-ATPase β-subunit. Binding was promoted by low concentrations of cold enterostatin but displaced by higher concentrations. The relationship between binding activity and feeding behavior was studied by examining the ability of a number of enterostatin analogs to affect β-casomorphin binding to the $F_1$-ATPase β-subunit. Peptides that suppressed food intake promoted β-casomorphin binding whereas peptides that stimulated food intake or did not affect the food intake displaced β-casomorphin binding. Surface plasmon resonance binding could be detected enterostatin to the beta subunit of $F_1$-ATPase complex with a Kd of 150 nM. Western blot analysis showed the $F_1$-ATPase β-subunit was present on plasma and mitochondrial membranes of rat liver, pancreas, and amygdala. The data provides evidence that the $F_1$-ATPase β-subunit is the enterostatin receptor and suggests that enterostatin and β-casomorphin bind to distinct sites on the protein.

We have discovered that enterostatin can cause the translocation of the $F_1$-ATPase beta subunit to the plasma membrane. This should increase the level of plasma membrane ATPase activity and regulate membrane functions and intracellular metabolism through changes in ATP, ADP or AMP concentrations. The initial demonstration utilized Green Fluorescent Protein (GFP)-tagged protein transfected into HepG2 cells, and showed that enterostatin induced a movement of the protein to the perimeter of cells. Since the available literature has identified this protein as present in the plasma membranes of a number, but not all, cell types, the ability to induce translocation of this protein to the plasma membrane will have a variety of biological effects depending upon the cell type. Increasing its presence in the plasma membranes of hepatocytes would increase binding to ApoA-1, regulating endocytosis of HDL particles, and affecting cholesterol transport; of lymphocytes would increase angiostatin binding affecting angiogenesis and tumor growth;

of endothelial cells would affect inflammatory responses or vascular integrity; and of pancreatic cells would modulate the inhibitory effect of enterostatin on insulin secretion. Thus, the ability to regulate the localization of enterostatin to the plasma membrane could regulate insulin secretion, cholesterol and lipid transport, angiogenesis and tumor growth.

MODES FOR CARRYING OUT THE INVENTION

It has been discovered that the ability of analogues to affect binding of a labeled β-casomorphin (an enterostatin antagonist (44, 52)) to recombinant rat $F_1$-ATPase β-subunit was closely correlated with their enterostatin-like biological activity. Using BiaCore Plasmon Resonance Spectroscopy, a Kd of 150 nM for enterostatin binding to the purified protein was found. Using immunohistochemistry and western blots, the presence of the $F_1$-ATPase β-subunit was demonstrated in plasma membranes of liver, pancreas and amygdala. To investigate the partitioning of the $F_1$-ATPase β-subunit into plasma membranes, HepG2 cells were transfected with either $F_1$-ATPase β-subunit-green fluorescent protein (GFP) or $F_1$-ATPase α-subunit-red fluorescent protein (RFP) constructs. The effects of enterostatin on the intracellular localization of the proteins were studied using deconvolution or confocal microscopy. Enterostatin did not alter the location of $F_1$-ATPase α-subunit-RFP but induced movement of the $F_1$-ATPase β-subunit-GFP to the periphery of cells. These studies, showing the plasma membrane localization of the $F_1$-ATPase β-subunit, the influence of enterostatin on the cellular location of the protein, the appropriate Kd value for binding, together with the previous correlation of binding effects with biological activity for a number of analogues, indicate that this protein is the enterostatin receptor. Further, the ATPase activity of the β-subunit indicates that enterostatin signals through changes in intracellular ATP levels.

EXAMPLE 1

Materials and Methods

Figure 1A:
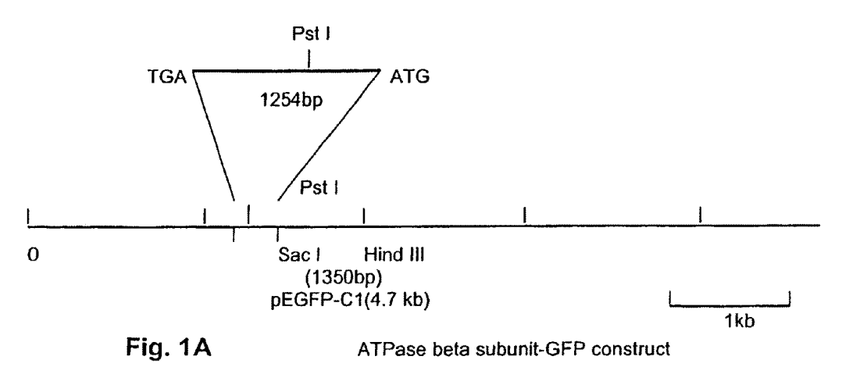
FIG. 1A illustrates the structure of the $F_1$-ATPase beta subunit—GFP construct.

Generation of $F_1$-ATPase beta subunit-GFP fusion protein. The $F_1$-ATPase β-subunit clone (1,254 bp) was generated by PCR from an amygdala cDNA library using $F_1$-ATPase β-subunit forward primer (5'GAGAG GAGCTCCACTATTGCTATGGATGGC3' (SEQ ID NO. 1), Sac I recognition site underlined) and $F_1$-ATPase β-subunit reverse primer (5'GAGAG AAGCTTCACGACCCATGCTC3' (SEQ ID NO. 2), Hind III recognition site underlined), according to procedures described in Appendix B. The PCR product was cloned into the pEGFP-C1 vector (Clonetech, Palo Alto, Calif.) between the Sac I and Hind III sites as shown in FIG. 1A. The construct was then transformed into DH5α cells. Transformants were screened and positive clones containing plasmid with the correct orientation of the insert were cultured.

Figure 1B:
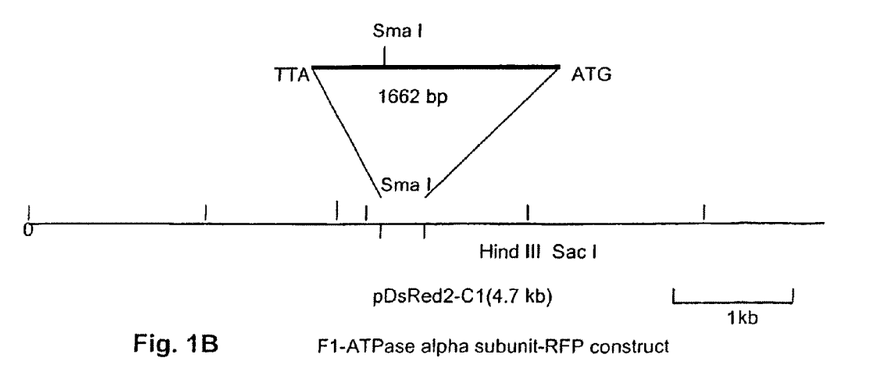
FIG. 1B illustrates the structure of the $F_1$-ATPase alpha subunit—RFP construct.

Generation of $F_1$-ATPase alpha subunit-RFP fusion protein. The $F_1$-ATPase α-subunit clone (1,662 bp) was generated by PCR from an amygdala cDNA library using $F_1$-ATPase α-subunit forward primer (5'GAGG GAGCTCAGCTGCAAGGATGCTGTCC3' (SEQ ID NO. 3), Sac I recognition site underlined) and $F_1$-ATPase α-subunit reverse primer (5' GAGAG AAGCTTTTACCGTTCAAACCCAGC3' (SEQ ID NO. 4), Hind III recognition site underlined). The PCR product was cloned into the pDsRed2-C1 vector (Clonetech) between the Sac I and Hind III sites as shown in FIG. 1B. The construct was then transformed into DH5α cells. Transformants were screened, and positive clones containing plasmid with the correct orientation of the insert were cultured.

Cell Culture and Transfection. Human liver cells (HepG2 cell line, Pennington Biomedical Research Center, Baton Rouge, La.) were grown and maintained in Dulbecco's modified eagle's medium (Gibco, Carlsbad, Calif.) containing 10% fetal bovine serum, penicillin (1,000 u/ml), and streptomycin (1,000 u/ml). For transient transfection experiments, the HepG2 cell line was seeded into 24-well plates (Corning, VWR, West Chester, Pa.) at 50-70% confluency. For each well of HepG2 cells, 0.8 μg of either the pATPase beta-GFP or pATPase alpha-RFP and 2.4 μl of Fugene6 (Roche, Indianapolis, Ind.) were incubated with 100 μl of Optimem (Gibco) for 30 min at room temperature. The cells were transfected using this mixture in 1 ml total volume for 16-18 h and visualized by microscopy 18-24 h after the transfection. For deconvolution microscopy (Zeiss Axioplan 2 imaging system, Thorrnwood, N.Y.), microscope cover slips (Fisher, Pittsburgh, Pa.) were pre-treated and placed in a 12-well plate. Cell culture and transfection procedures on glass slides were the same as described above. To image the live cells in real time, cells were cultured in the Lab-Tek II chambered coverglass (Nalge Nunc International, Rochester, N.Y.), and were observed using a confocal microscope (Zeiss NSM 510 META) with an inverted camera.

EXAMPLE 2

Enterostatin Alters $F_1$-ATPase Beta Subunit Cell Location in HepG2 Cells

Either 0.5 or 2 µM enterostatin was added to the HepG2 cells after transfection with either alpha subunit-RFP or beta subunit-GFP for 16-18 hrs. After incubation with enterostatin for 15, 30, or 60 min, the cover slide was removed from the well and placed on a glass slide. Protein expression in HepG2 cells was then observed using deconvolution microscopy.

Figure 2A:
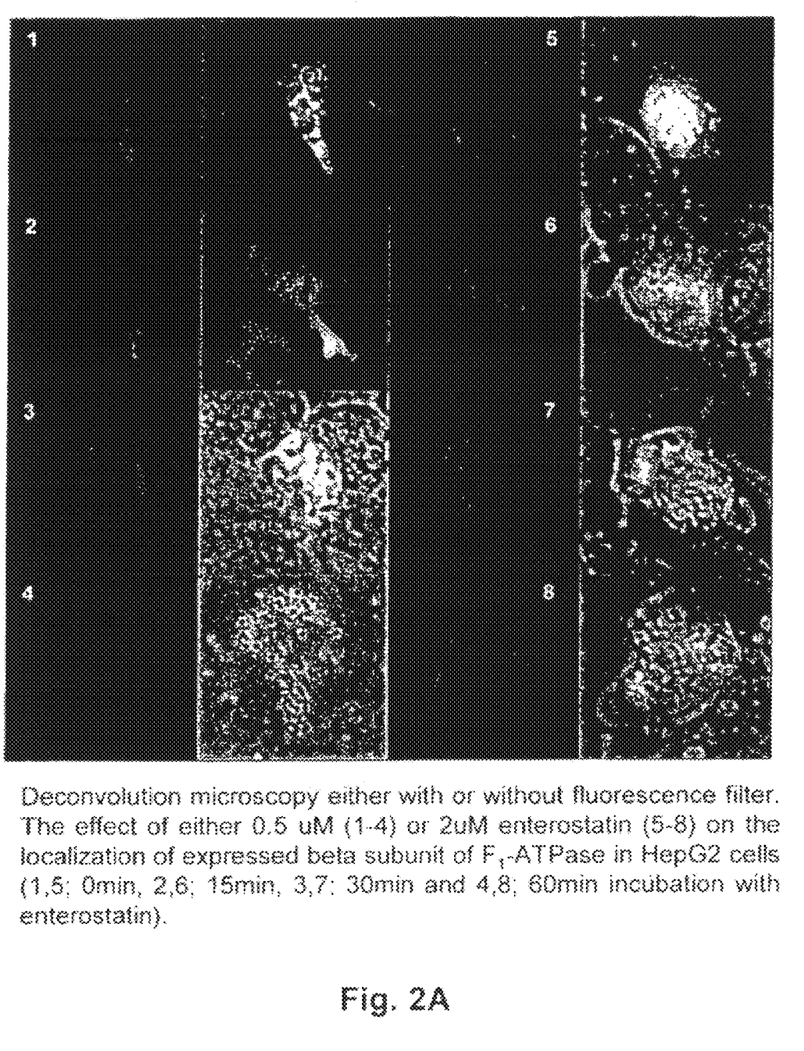
FIG. 2A illustrates micrographs from deconvolution microscopy with and without a fluorescence filter when viewing HepG2 cells transformed with the $F_1$-ATPase beta subunit—GFP construct treated with either 0.5 μM (Panels 1-4) or 2 μM (Panels 5-8) enterostatin for 0 min (Panels 1 and 5), 15 min (Panels 2 and 6), 30 min (Panels 3 and 7), and 60 min (Panels 4 and 8).
Figure 2B:
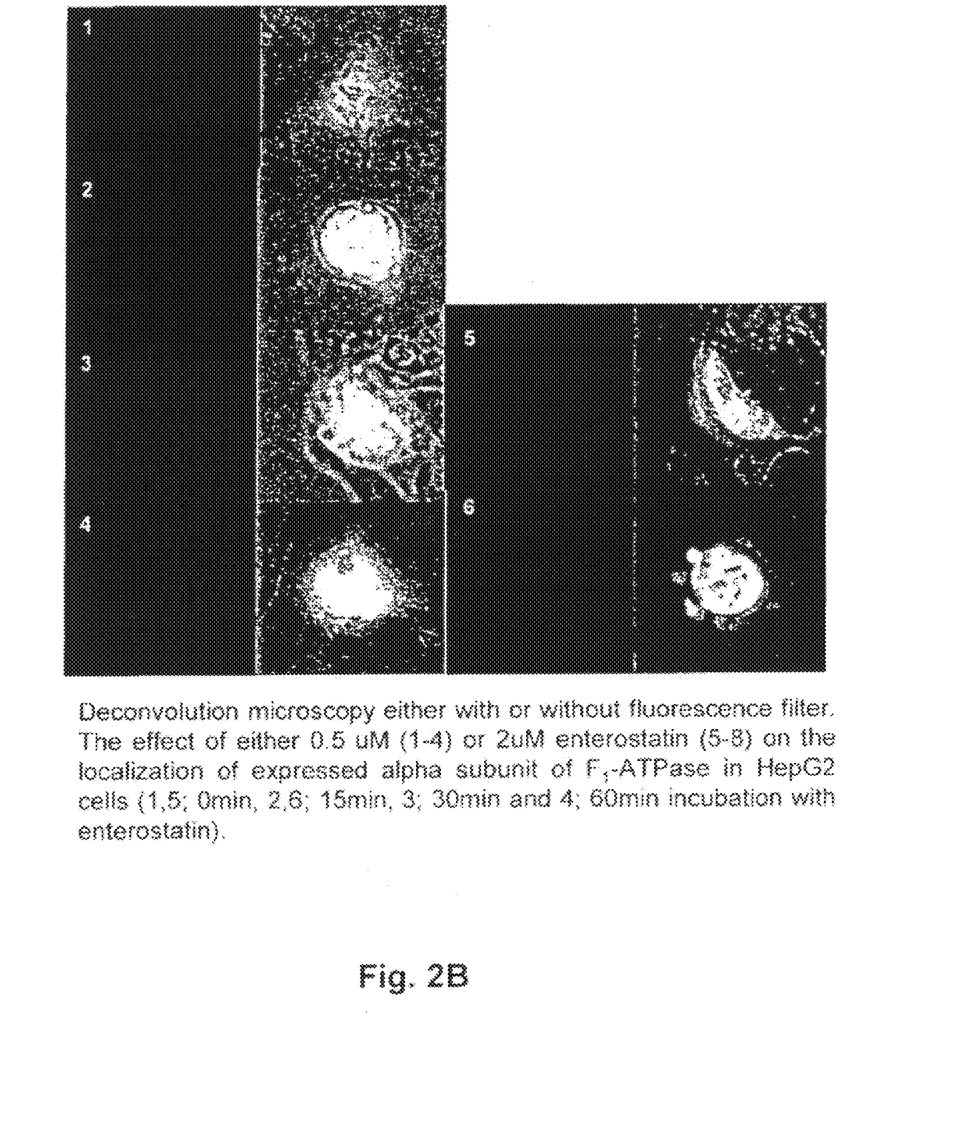
FIG. 2B illustrates micrographs from deconvolution microscopy with and without a fluorescence filter when viewing on HepG2 cells transformed with the $F_1$-ATPase alpha subunit—RFP construct treated with either 0.5 μM (Panels 1-4) or 2 μM (Panels 5-8) enterostatin for 0 min (Panels 1 and 5), 15 min (Panels 2 and 6), 30 min (Panel 3), and 60 min (Panel 4).
Figure 3A:
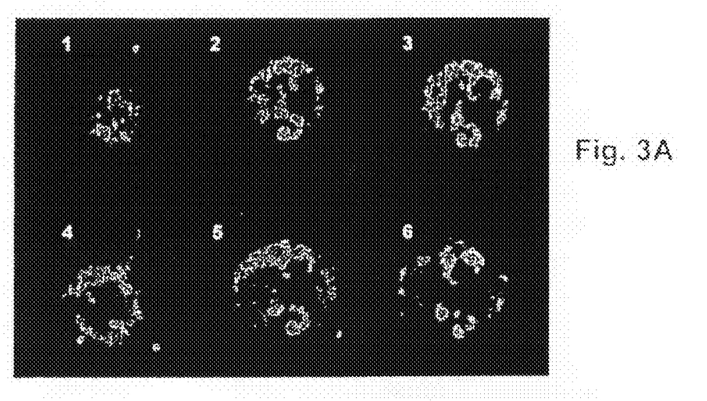
FIG. 3A illustrates micrographs from confocal microscopy when viewing HepG2 cells transformed with the $F_1$-ATPase beta subunit—GFP construct treated with 2 μM enterostatin for 0 min (Panels 1, 2 and 3) and 75 min (Panels 4, 5, and 6).
Figure 3B:
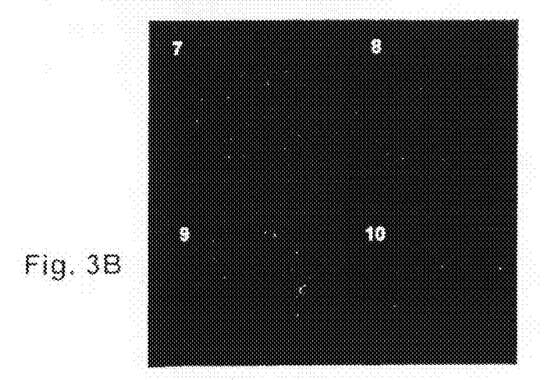
FIG. 3B illustrates micrographs from confocal microscopy when viewing HepG2 cells transformed with the $F_1$-ATPase alpha subunit—RFP construct treated with 2 μM enterostatin for 0 min (Panels 7 and 8) and 40 min (Panels 9 and 10).

Enterostatin did not change the distribution of expressed $F_1$-ATPase alpha subunit-RFP in HepG2 within the time of incubation with either concentration of enterostatin (FIG. 2B). However, after incubation with both 0.5 and 2 uM enterostatin, $F_1$-ATPase beta subunit-GFP was clearly relocated toward the cell periphery (FIG. 2A). To study this event in real time, a confocal microscope with an inverted camera was used to observe protein localization in transfected HepG2 cells at the different incubation times with 2 µM enterostatin for both the beta subunit of $F_1$-ATPase (FIG. 3A) and the alpha subunit of $F_1$-ATPase (FIG. 3B).

EXAMPLE 3

$F_1$-ATPase Beta Subunit in Plasma Membrane of Liver, Pancreas and Amygdala Cells Using Western blot analysis and immunohistochemistry, $F_1$-ATPase β-Subunit was discovered present in the plasma membrane and mitochondrial membranes of liver, pancreas and amygdala cells from rats. The purified $F_1$-ATPase β-Subunit (200 µg/ml) (produced as described in Appendix B) in Freunds complete adjuvant (Sigma Chemical Co., St. Louis, Mo.) was injected subcutaneously at multiple sites on the back of New Zealand white rabbits. Booster doses, diluted into Freunds incomplete adjuvant, were administered at weeks 4, 8 and 12. Blood was collected from injected animals on weeks 0, 4, 8, and 12. Rabbit antiserum was prepared by centrifugation (2000×g, 30 min, 4° C.) and stored at −20° C. in aliquots. The antibody was purified by passing over a protein A bead column (Sigma Chemical Co.). The antibody dilution necessary for antigen detection was assayed by an ELISA. Ninety six-well plates were coated with 100 ng/well of purified $F_1$-ATPase β-Subunit in sodium carbonate buffer (pH 9.6) and incubated overnight at 4° C. The primary and secondary antibodies used were as described below.

The ability of the antibody to detect the purified $F_1$-ATPase β-subunit was shown using an immunoblot technique. Purified proteins were transferred onto polyvinylidene fluoride membranes and incubated with the anti-rabbit rat $F_1$-ATPase beta subunit antibody (1:1000) as a primary antibody and an anti-rabbit IgG peroxidase goat antibody (1:2000; Sigma Chemical Co.) as a secondary antibody. Immune complexes were visualized using the ECL Western blotting detection system (Amersham, Buckinghamshire, United Kingdom). As a negative control, the primary antibody was replaced with a non-immune rabbit IgG.

To prepare plasma membrane fractions, liver, amygdala, and pancreas tissues were separately extracted from rats and washed three times with 200 µl of extraction buffer on ice (10 mM HEPES, pH 7.5, containing 200 mM mannitol, 70 mM sucrose, and 1 mM EGTA) before homogenization. The washed tissue was homogenized in 10 volumes of ice-cold homogenization buffer (extraction buffer containing Mini-complete protease cocktail to final concentration of 0.5 mg/ml, [Roche, Indianapolis, Ind.]) using a Potter-Elvehjem Teflon-glass homogenizer. The homogenates were centrifuged at 600 g for 5 min at 4° C., the supernatants removed, and then centrifuged at 16,000 g for 20 min at 4° C. to yield the predominantly mitochondrial fraction. The 16,000 g supernatants containing plasma membrane and cytosolic components were centrifuged at 100,000 g for 1 hr at 4° C. to sediment the plasma membrane fractions. The fractions-containing the plasma membrane and the mitochondrial membrane were checked for purity using the marker enzymes alkaline phosphatase and cytochrome c oxidase respectively (Sigma Chemical Co., St Louis, Mo.). The purified membrane fractions were then tested for presence of $F_1$-ATPase β-subunit using the antibody described above in a Western blot analysis.

Figure 4A:
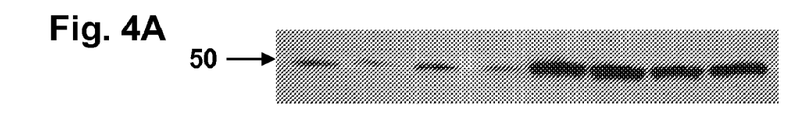
FIG. 4A illustrates the results of a Western blot analysis showing the location of $F_1$-ATPase β-subunit in rat amygdala cells in both the plasma membrane (PM) and mitochondrial membrane (MT).
Figure 4B:
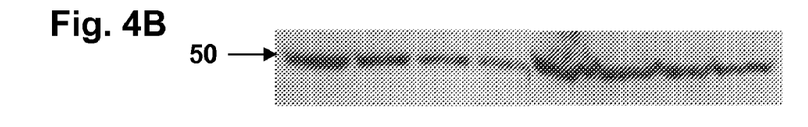
FIG. 4B illustrates the results of a Western blot analysis showing the location of $F_1$-ATPase β-subunit in rat liver cells in both the plasma membrane (PM) and mitochondrial membrane (MT).
Figure 4C:
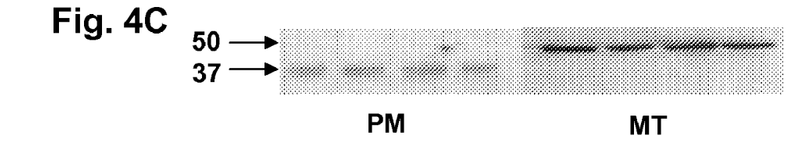
FIG. 4C illustrates the results of a Western blot analysis showing the location of $F_1$-ATPase β-subunit in rat pancreas cells in both the plasma membrane (PM) and mitochondrial membrane (MT).
Figure 4D:
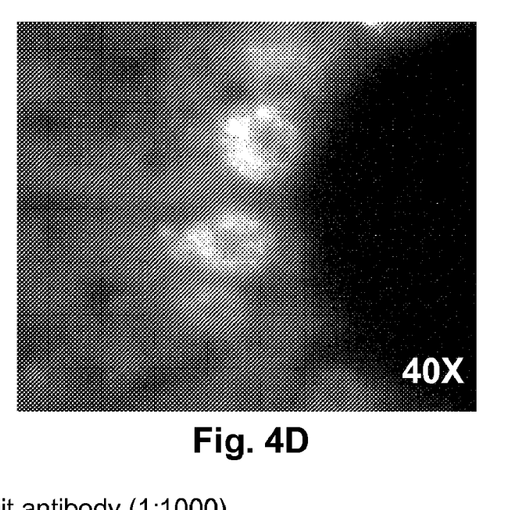
FIG. 4D illustrates the results of immunohistochemistry analysis showing the location of $F_1$-ATPase β-subunit in rat liver cells in the plasma membrane (PM).

The results for amygdala, liver, and pancreas are shown respectively in FIGS. 4A, 4B, and 4C. The $F_1$-ATPase β-subunit was shown to be present in all three tissues, in both the plasma membrane and the mitochondrial membrane. This is the first report of the presence of this enzyme in the plasma membrane of brain and pancreatic cells. The lower molecular size of the $F_1$-ATPase β-subunit in pancreatic plasma membrane as shown in FIG. 4C may reflect either some proteolysis during tissue homogenization or that the protein occurs naturally in a cleaved (shorter) form in the plasma membrane of pancreatic cells. FIG. 4D indicates the presence of the $F_1$-ATPase β-subunit in the plasma membrane of liver cells using immunohistochemistry. FIG. 4D was obtained using conventional immunohistochemistry using a primary antibody to the $F_1$-ATPase β-subunit and a secondary antibody to rabbit IgG coupled to horseradish peroxidase.

EXAMPLE 4

Diagnostic Test to Measure the Effectiveness of Enterostatin Treatment

Lymphocytes will be collected from human subjects and used to assay the level of plasma membrane ATPase activity and the increase in plasma membrane $F_1$-ATPase β-subunit in response to enterostatin. It is believed that lymphocytes are a good indicator of the relative localization of this protein to plasma membranes due to the presence of enterostatin in other body tissues, and of the ATPase activity of this protein.

The change in enterostatin-related ATPase activity with time will be used as an index of the ability of enterostatin to promote translocation of the protein into the plasma membranes of other tissues, e.g., liver or pancreas. Lymphocyte cell-surface ATPase activity will be assayed using $[\alpha\text{-}^{32}P]$ ATP as substrate and assaying for the production of ADP. Freshly prepared lymphocytes will be incubated with or without enterostatin for 30 min and then assayed for cell surface ATPase activity. The difference in activity will reflect the level of $F_1$-ATPase β-subunit translocated into the membrane in response to enterostatin. This assumption will be validated using lymphocytes transfected with beta subunit F1 ATP synthase-green fluorescent protein construct, and visually measuring the level of translocation by confocal microscopy. This level of translocation will then be correlated with changes in cell surface ATPase activity.

After validation of the assay, lymphocytes will be prepared from a cross section of human subjects that will include lean healthy individuals, metabolic syndrome subjects, moderately and severely obese individuals. We hypothesize that lymphocyte cell surface ATPase activity will be negatively correlated with cholesterol levels, Body Mass Index and with the anorectic response to enterostatin. We also believe that the lymphocyte $F_1$-ATPase β-subunit increase due to enterostatin will be correlated with the effectiveness of treating the individual with enterostatin. Thus this assay will be used to identify individuals who would benefit from enterostatin therapy.

EXAMPLE 5

Identification of Agonists/Antagonists of Enterostatin

To identify other small molecules, compounds or enterostatin agonists/antagonists that alter the partitioning of the $F_1$-ATPase β-subunit into the plasma membrane, a number of experiments will be conducted in a variety of cell lines.

Insulin-secreting cells. INS-1 cells shall be used that sensitive or resistant to glucagons-like peptide 1 (GLP-1) and glucose. GLP-1 is an insulin secretion stimulating peptide. Additional cell types lacking receptors for other peptides could be used. These cells will be transfected with beta subunit ATP synthase-green fluorescent protein (BATPS-GFP) construct. The effects of enterostatin, enterostatin analogues (examples are given in Table 1 in Appendix B), enterostatin agonists and antagonists, and other small molecule compounds will be studied on the movement of the $F_1$-ATPase β-subunit protein into the plasma membrane. The ability to compartmentalize the protein to the plasma membrane will be correlated with changes in cellular ATP levels and the effects of enterostatin or other secretagogues on insulin secretion.

HepG2 cells or primary hepatocytes cultures. HepG2 or primary hepatocyte cells will be used to show that enterostatin regulates high density lipoprotein (HDL) uptake and cholesterol transport through the promotion of translocating beta subunit ATP synthase into the plasma membrane. We shall show that enterostatin increases the binding of $^{125}$I-labelled free Apo A1 to plasma membranes from HepG2 cells, and that this binding is correlated with an increase in ATPase activity and ADP production inside the cell, and that the effect is absent when the cells are stimulated by ADP. Further we shall show that the ability of enterostatin to promote these events is increased when the concentration of the $F_1$-ATPase β-subunit in plasma membranes is increased. The amount of the $F_1$-ATPase β-subunit in the plasma membranes will be measured using the BATPS-GFP construct as described above.

Human endothelial cells. Human endothelial cells derived from umbilical veins or other sources will be used to study the effect of enterostatin on angiogenesis. The ability to bind angiostatin will be correlated with the level of beta subunit F1 ATPsynthase in the plasma membranes, and the co-localization of angiostatin and enterostatin binding shown by confocal immunofluorescent microscopy. Further, the effect of transfection of BATPS-GFP construct on these functions will be studied. The effects of enterostatin on vessel proliferation in an in vitro assay of adipose tissue angiogenesis will also be studied. We expect enterostatin will inhibit angiogenesis since incorporation of the $F_1$-ATPase β-subunit into the plasma membrane will reduce the ability of angiostatin to bind to the $F_1$-ATPase α-subunit.

Cancer cells. The effects of enterostatin on the response of cancer cells to hypoxic challenge will be studied. Either breast cancer or prostate cancer tumor cell lines will be used to show that enterostatin affects apoptosis markers and/or cell survival, and that this effect is related to the level of plasma membrane $F_1$-ATPase β-subunit. Cells will also be transfected with the BATPS-GFP construct to show that enterostatin induces movement of the protein into the plasma membrane fraction and that this translocation influences cell survival and apoptosis. These transfected cells could also be used to search for small molecule agonists/antagonists or mimetics of enterostatin. We expect enterostatin to increase apoptosis and death of cancer cells because of its effects on angiostatin binding as discussed above.

Miscellaneous

The term "enterostatin" used herein and in the claims refers to the peptide enterostatin, its derivatives and analogs. The terms "derivatives" and "analogs" are understood to be compounds that are similar in structure to enterostatin and that exhibit a qualitatively similar effect to the unmodified enterostatin. Examples of such derivatives and analogs can be found in Appendix B, Table 1.

The term "enterostatin agonist" as used herein refers to a molecule that selectively increases the translocation of the $F_1$-ATPase β-subunit into the plasma membrane of certain mammalian tissues in which enterostatin increases the translocation. An agonist can act by any mechanism, such as binding the $F_1$-ATPase β-subunit at the normal enterostatin binding site, thereby mimicking enterostatin and promoting receptor signaling. As used herein, enterostatin agonist can include mimetics of enterostatin. An enterostatin agonist can also act, for example, by increasing the binding ability of enterostatin, or by favorably altering the conformation of the enterostatin receptor.

The term "enterostatin antagonist" as used herein refers to a compound that selectively inhibits or decreases the translocation of the $F_1$-ATPase β-subunit into the plasma membrane in tissues in which enterostatin would increase the translocation. An antagonist can act by any antagonistic mechanism, such as by binding to enterostatin or to $F_1$-ATPase β-subunit, thereby inhibiting binding between enterostatin and the $F_1$-ATPase β-subunit. An enterostatin antagonist can also act indirectly, for example, by modifying or altering the native conformation of either enterostatin or $F_1$-ATPase β-subunit.

The term "therapeutically effective amount" as used herein refers to an amount of enterostatin or its analogs, or its agonists or antagonists, sufficient to change the amount of F1-ATPase beta subunit in the plasma membrane of mammalian cells to a statistically significant degree (p<0.05). The dosage ranges for the administration of enterostatin, its analogs or antagonist are those that produce the desired effect. Generally, the dosage will vary with the age, weight, condition, sex of the patient, and type of cell. A person of ordinary skill in the art, given the teachings of the present specification, may readily determine suitable dosage ranges. The dosage can be adjusted by the individual physician in the event of any contraindications. In any event, the effectiveness of treatment can be determined by monitoring the level of $F_1$-ATPase beta subunit in the plasma membrane methods well known to those in the field. Moreover, enterostatin, its analogs, agonists, or antagonists can be applied in pharmaceutically acceptable carriers known in the art. The application can be oral, by injection, or topical, providing that in an oral administration the compounds are preferably protected from digestion.

The complete disclosures of all references cited in this application are hereby incorporated by reference. Also, incorporated by reference is the complete disclosure of the following documents: M. Park et al., "The $F_1$-ATPase β-subunit is the putative enterostatin receptor," Peptides, vol. 25, pp. 2127-33; available online 19 Oct. 2005; and M. Park et al. "Enterostatin regulates partitioning of its receptor, the $F_1$-ATPase β-subunit into plasma membranes," a poster presented at the North American Association for the Study of Obesity, Las Vegas, Nev., on Nov. 15, 2004. In the event of an otherwise irreconcilable conflict, however, the present specification shall control.

REFERENCES

1. Barton C., L. Lin, D. A. York and G. A. Bray. Differential effects of enterostatin, galanin and opioids on high-fat diet consumption. *Brain Res.* 702:55-60, 1995
2. Berger K, Sivars U, Winzell M S, Johansson P, Hellman U, Rippe C, and Erlanson-Albertsson C. Mitochondrial ATP synthase—a possible target protein in the regulation of energy metabolism in vitro and in vivo. *Nutr Neurosci* 2002; 5: 201-210.
3. Berger K, Winzell M S, Erlanson-Albertsson C. Binding of enterostatin to the human neuroepithelioma cell line SK-N-MC. *Peptides* 19: 1525-1531, 1998.
4. Bowyer, R. C., Rowston, W. M., Jehanli, A. M. T., Lacey, J. H., Hermon-Taylor, J., The effect of a satiating meal on the concentrations of procolipase activation peptide in the serum and urine of normal and morbidly obese individuals, *Gut.,* 34, 1520-1525, 1993.
5. Chang S, Park S, Kim S and Kang C. Interaction of the C-terminal domain of p43 and the α-subunit of ATP synthase: its functional implication in endothelial cell proliferation. *J. Biol. Chem.* 277; 8388-8394, 2001.
6. Das B, Mondrogan M. O., Sadeghian M, Hatcher V B and Norin A J. A novel ligand in lymphocyte mediated cytotoxicity: expression of beta subunit of H+ transporting ATP synthase on the surface of tumor cell lines. *J. Exp. Med.* 180: 273-81, 1994
7. Erlanson-Albertsson, C., Jie, M., Okada, S., York, D., Bray, G. A., Pancreatic procolipase propeptide, enterostatin, specifically inhibits fat intake, *Physiol. Behav.,* 49, 1191-1194, 1991.
8. Erlanson-Albertsson, C., Larsson, A., A possible physiological function of procolipase activation peptide in appetite regulation, *Biochimie,* 70, 1245-1250, 1988.
9. Erlanson-Albertsson, C., York, D., Enterostatin—A peptide regulating fat intake, *Obesity Res,* 5, 360-372, 1997.
10. Halford J, Smith B K, Blundell J. Serotonin (5HT) and serotonin receptors in the regulation of macronutrient intake In: Neural and Metabolic Control of Macronutrient intake eds H R Berthoud and R J Seeley, pp 425-446 CRC Press, Boca Raton. 2000.
11. Imamura, M., Sumar, N., Hermon-Taylor, J., Robertson, H. J. F., Prasad, C., Distribution and characterization of enterostatin-like immunoreactivity in human cerebrospinal fluid. *Peptides,* 19: 1385-91, 1998.
12. Lin L, Braymer H D and York D A. Procolipase gene and enterostatin expression in the rat brain. *FASEB J;* 2002; A783.
13. Lin L, S. R. Thomas, G. Kilroy, G. J. Schwartz and D. A. York. The enterostatin inhibition of dietary fat intake is dependent upon CCKA receptors. *Am. J. Physiology* August; 285(2):R321-8, 2003.
14. Lin L., D. A. York. Amygdala enterostatin induces c-Fos expression in regions of hypothalamus that innvervate the PVN; *Brain Res.* 2004 Sep. 10; 1020(1-2):147-53.
15. Lin, L., Chen, J., York, D. A., Chronic icv enterostatin preferentially reduced fat intake and lowered body weight, *Peptides,* 18, 657-661, 1997.
16. Lin, L., G. Bray, and D. A. York. Enterostatin suppresses food intake in rats after near celiac and intracarotid arterial injection. *Am. J. Physiol. Reg Integr Comp Physiol.* 2000 May; 278(5):R1346-51.
17. Lin, L., Gehlert, D. R., York, D. A., Bray, G. A., Effect of enterostatin on the feeding responses to galanin and NPY, *Obes. Res.,* 1, 186-192, 1993.
18. Lin, L., Umahara, M. York, D. A., Bray, G. A., β-casomorphins stimulate and enterostatin inhibits the intake of dietary fat in rats. *Peptides,* 19, 325-331, 1998.
19. Lin, L., York, D. A., Enterostatin actions in the amygdala and PVN to suppress feeding in the rat, *Peptides,* 18, 1341-1347, 1997.
20. Lin, L., York, D. A., Changes in the microstructure of feeding after administration of enterostatin into the paraventricular nucleus and the amygdala, *Peptides,* 19, 557-562, 1998.
21. Lin, L., York, D. A., Comparisons of the effects of enterostatin on food intake and gastric emptying in rats, *Brain Res,* 745, 205-209, 1997.
22. Lin, L., Okada, S., York, D. A., Bray, G. A., Structural requirements for the biological activity of enterostatin, *Peptides,* 15, 849-854, 1994.
23. Martinez L O, Jacquet S, Esteve J P, Rolland C, Cabezon E, Champagne E, Pineau T, Georgeaud V, Walker J E, Terce F, Collet X, Perret B, and Barbaras R. Ectopic beta-chain of ATP synthase is an apolipoprotein A-I receptor in hepatic HDL endocytosis. *Nature* (Lond) 2003; 421: 75-79.
24. Mei J, Bourras M, Erlanson-Albertsson C. Inhibition of insulin by intraduodenally infused VPDPR in rats. *Peptides* 18: 651-657, 1997
25. Mei, J., Bowyer, R. C., Jehanli, A. M. T., Patel, G., Erlanson-Albertsson, C., Identification of enterostatin, the pancreatic procolipase activation peptide, in the intestine of rat: effect of CCK-8 and high-fat feeding, *Pancreas,* 8, 488-493, 1993.
26. Mei, J., Cheng, Y., Erlanson-Albertsson, C., Enterostatin—its ability to inhibit insulin secretion and to decrease high-fat food intake, *Int. J. Obesity,* 17, 701-704, 1993.
27. Mei, J., Erlanson-Albertsson, C., Effect of enterostatin given intravenously and intracerebroventricularly on high-fat feeding in rats, *Regul. Pept.,* 41, 209-218, 1992
28. Mei, J., Erlanson-Albertsson, C., Plasma insulin response to enterostatin and effect of adrenalectomy in rat, *Obes. Res.,* 4, 513-519, 1996.
29. Mei, J., Erlanson-Albertsson, C., Role of intraduodenally administered enterostatin in rat: inhibition of food intake, *Obes. Res.,* 4, 61-165, 1996.
30. Miner, J. L., Erlanson-Albertsson, C., Paterson, J. A., Baile, C. A., Reduction of feed intake in sheep by enterostatin, the procolipase activation peptide, *J. Anim. Sci.,* 72, 1578-1582, 1994.
31. Moser t ET AL Angiostatin binds ATP synthase on the surface of human endothelial cells. *Proc. Natl. Acad. Sci.* 96: 2811-2816, 1999
32. Nagase H, A. Nakajimia, H. Sekihara, D. A. York and G. A. Bray. Regulation of feeding behavior, gastric emptying, and sympathetic nerve activity to interscapular brown adipose tissue by galanin and enterostatin: the involvement of vagal-central nervous system interactions. *J. Gastroenterol. November;* 37 Suppl 14:118-27, 2002.
33. Nagase H., G. A. Bray and D. A. York. Effect of galanin and enterostatin on sympathetic nerve activity to interscapular brown adipose tissue. *Brain Res.* 709:44-50, 1996.
34. Okada S., D. A. York and G. A. Bray. Procolipase mRNA: Tissue localization and effects of diet and adrenalectomy. Biochem. J. 292:787-789, 1993

35. Okada, S., Lin, L., York, D. A., Bray, G. A., Chronic effects of intracerebral ventricular enterostatin in Osborne-Mendel rats fed a high-fat diet, *Physiol. Behav.,* 54, 325-330, 1993.
36. Okada, S., York, D. A., Bray, G. A., Mei, J., Erlanson-Albertsson, C., Differential inhibition of fat intake in two strains of rat by the peptide enterostatin, *Amer. J. Physiol.,* 262, R1111-R1116, 1992.
37. Okada, S., York, D. A., Bray, G. A., Erlanson-Albertsson, C., Enterostatin (Val-Pro-Asp-Pro-Arg) the activation peptide of procolipase selectively reduces fat intake, *Physiol. Behav.,* 49, 1185-1189, 1991.
38. Ookuma, K. C., Barton, C., York, D. A., Bray, G. A., Effect of enterostatin and kappa-opioids on macronutrient selection and consumption, *Peptides,* 18, 785-791, 1997.
39. Ookuma, M. and D. A. York. Inhibition of insulin release by enterostatin. *Int. J. Obesity* 22:800-805, 1998.
40. Pierzynowski, S. G., Erlanson-Albertsson, C., Podgumiak, P., Kiela, P., Westrom, B., Possible integration of the electrical activity of the duodenum and pancreas secretion through enterostatin, *Biomed. Res.,* 15, 257-260, 1994.
41. Rippe, C, berger K, Boiers C, Ricquier D and Erlanson-Albertsson C. Effect of high fat diet, surrounding temperature and enterostatin on uncoupling protein gene expression. *Am. J. Physiol.* 279; E293-E300, 2000.
42. Rodriguez-Gallardo J, Silvestre R A, Marco J Inhibitory effect of enterostatin on the beta cell response to digestive insulinotropic peptides. *Int J Obes Relat Metab Disord* 23(8):787-92, 1999
43. Rössner, S., Barkeling, B., Erlanson-Albertsson, C., Larsson, P., Wahlin-Boll, E., Intravenous enterostatin does not affect single meal food intake in man, *Appetite,* 34, 37-42, 1995.
44. Smeets, M., P. Geiselman, G. A. Bray and D. A. York. The effect of oral enterostatin on hunger and food intake in human volunteers. *FASEB J* 13(5):A871, 1999 (Abs).
45. Smith B. K., D. A. York, and G. A. Bray. Chronic d-fenfluramine treatment reduces fat intake independent of macronutrient preference. *Pharmacology Biochem. & Behavior.* 60:105-114, 1998.
46. Sorhede, M., Rippe, C., Mulder, H., Erlanson-Albertsson, C., Enterostatin is produced in three different forms in the rat intestine, *Int. J Obesity,* 19, 115, 1995.
47. Tadayyon M., S Liou, C P Briscoe, G Badman, D S Eggleston, J R S Arch, D A York. Structure-function studies on enterostatin inhibition of insulin release. *Intl J Diabetes & Metabolism* 10:14-21, 2002.
48. Takenaka Y, Nakamura F, Yamamoto T, and Yoshikawa M. Enterostatin (VPDPR) and its peptide fragment DPR reduce serum cholesterol levels after oral administration in mice. *Biosci. Biotechnol. Biochem.* 2003; 67: 1620-1622.
49. Tian, Q., Nagase, H., York, D. A., Bray, G. A., Vagal-central nervous system interactions modulate the feeding response to peripheral enterostatin, *Obes. Res.,* 2, 527-534, 1994.
50. Townsley, M. I., Erlanson-Albertsson, C., Ohlsson, A., Rippe, C., Reed, R. K, Enterostatin efflux in cat intestinal lymph: Relation to lymph flow, hyaluronan and fat absorption, *Am. J. Physiol.,* 271, G714-G721, 1996.
51. Weatherford, S. C., Lattemann, D. F., Sipols, A. J., Chavez, M., Kermani, Z. R., York, D. A., Bray, G. A., Porte, Jr., D. Woods, S. C., Intraventricular administration of enterostatin decreases food intake in baboons, *Appetite,* 19, 225, 1992.
52. White C L, Bray G A, and York D A. Intragastric beta-casomorphin(1-7) attenuates the suppression of fat intake by enterostatin. *Peptides* 2000; 21: 1377-1381.
53. Winzell, M. S., M. E. Lowe, and C. Erlanson-Albertsson. Rat gastric procolipase: sequence, expression, and secretion during high-fat feeding. *Gastroenterology* 115: 1179-1185, 1998.
54. Wu, Y J, D Hughes, L Lin, DH Braymer and DA York. Comparative study of enterostatin sequence in five rat strains and enterostatin bind proteins in rat and chicken serum. *Peptides* March; 23: 537-544, 2002.
55. York, D. A, Waggener, J., Bray, G. A., Brain amine responses to peripheral enterostatin, *Int. J. Obes.,* 18, 102, 1994 (Abs.).
56. York, D. A. and Lin L. Enterostatin: A peptide regulator of fat ingestion. In: Pennington Symposium Series, Molecular Biology of Obesity, Vol. 4, pp. 281-297 (G. A. Bray and D. Ryan, eds.), Louisiana State University Press. Baton Rouge, USA, 1996.
57. York, D. A., L. Lin, B. Smith, J. Chen. Enterostatin as a regulator of fat intake. In: Neural and metabolic control of macronutrient selection. H. R. Berthoud and R. J. Seeley (eds.), Chap 20, pp 295-308, 2000. CRC Press (Boca Raton, USA).
58. York, D. A., L. Lin, B. Smith, J. Chen. Enterostatin as a regulator of fat intake. In: Neural and Metabolic Control of Macronutrient Intake, H. Berthoud, R. Seeley (eds.), Chap. 20, pp 295-308, Boca Raton, Fla.: CRC Press, 2000.

What is claimed:

1. A method of measuring the activity of a compound as an enterostatin agonist or antagonist, said method comprising the sequential steps of:
   a. Contacting an in vitro mammalian cell with the compound in the presence of enterostatin under conditions wherein enterostatin will increase the amount of $F_1$-ATPase β-subunit in the plasma membrane of the cell to a known level, and
   b. Measuring the resulting concentration of $F_1$-ATPase β-subunit in the plasma membrane,
   Wherein an increased level of $F_1$-ATPase β-subunit in the plasma membrane above the known level due to enterostatin alone indicates that the compound possesses activity as an enterostatin agonist and wherein a decreased level of $F_1$-ATPase β-subunit in the plasma membrane below the known level due to enterostatin alone indicates that the compound possesses activity as an enterostatin antagonist.

2. A method of measuring the activity of a compound as an enterostatin agonist, said method comprising the sequential steps of:
   a. Contacting an in vitro mammalian cell with the compound in the presence of enterostatin under conditions wherein enterostatin will increase the amount of $F_1$-ATPase β-subunit in the plasma membrane of the cell to a known level, and
   b. Measuring the resulting concentration of $F_1$-ATPase β-subunit in the plasma membrane,
   Wherein an increased level of $F_1$-ATPase β-subunit in the plasma membrane above the known level due to enterostatin alone indicates that the compound possesses activity as an enterostatin agonist.

3. A method of measuring the activity of a compound as an enterostatin antagonist, said method comprising the sequential steps of:
   a. Contacting an in vitro mammalian cell with the compound in the presence of enterostatin under conditions wherein enterostatin will increase the amount of $F_1$-ATPase β-subunit in the plasma membrane of the cell to a known level, and
   b. Measuring the resulting concentration of $F_1$-ATPase β-subunit in the plasma membrane,
   Wherein a decreased level of $F_1$-ATPase β-subunit in the plasma membrane below the known level due to enterostatin alone indicates that the compound possesses activity as an enterostatin antagonist.

4. A method for assaying the responsiveness of a mammalian patient to a compound selected from the group consisting of enterostatin, enterostatin agonists, and enterostatin antagonists; said method comprising the steps of:
   a. Isolating from the patient cells selected from the group consisting of liver cells, brain cells, pancreatic cells, lymphocytes, and endothelial cells;
   b. Administering a therapeutically effective amount of the compound to the isolated cells in vitro; and
   c. Measuring the amount of $F_1$-ATPase β-subunit in the plasma membrane of the isolated cells.

5. A method as recited in claim 4, wherein the cells comprise lymphocytes, and wherein the compound comprises enterostatin.

* * * * *

SEQUENCE LISTING

<160> NUMBER OF SEQ ID NOS: 4

<210> SEQ ID NO 1
<211> LENGTH: 30
<212> TYPE: DNA
<213> ORGANISM: Artificial sequence
<220> FEATURE:
<223> OTHER INFORMATION: Synthetic Primer

<400> SEQUENCE: 1
gagaggagct ccactattgc tatggatggc        30

-continued

```
<210> SEQ ID NO 2
<211> LENGTH: 25
<212> TYPE: DNA
<213> ORGANISM: Artificial sequence
<220> FEATURE:
<223> OTHER INFORMATION: Synthetic primer

<400> SEQUENCE: 2
gagagaagct tcacgaccca tgctc                                              25

<210> SEQ ID NO 3
<211> LENGTH: 29
<212> TYPE: DNA
<213> ORGANISM: Artificial sequence
<220> FEATURE:
<223> OTHER INFORMATION: Synthetic primer

<400> SEQUENCE: 3
gagggagctc agctgcaagg atgctgtcc                                          29

<210> SEQ ID NO 4
<211> LENGTH: 29
<212> TYPE: DNA
<213> ORGANISM: Artificial sequence
<220> FEATURE:
<223> OTHER INFORMATION: Synthetic primer

<400> SEQUENCE: 4
gagagaagct tttaccgttc aaacccagc                                          29
```